United States Patent
Janik et al.

(10) Patent No.: US 10,247,663 B2
(45) Date of Patent: Apr. 2, 2019

(54) ONLINE LINEARIZATION OF AN OPTICAL SENSOR

(71) Applicant: B. BRAUN AVITUM AG, Melsungen (DE)

(72) Inventors: Waldemar Janik, Melsungen (DE); Jens Duru, Bebra (DE)

(73) Assignee: B. Braun Avitum AG, Melsungen (DE)

( * ) Notice: Subject to any disclaimer, the term of this patent is extended or adjusted under 35 U.S.C. 154(b) by 0 days.

(21) Appl. No.: 15/972,829

(22) Filed: May 7, 2018

(65) Prior Publication Data

US 2018/0328839 A1 Nov. 15, 2018

(30) Foreign Application Priority Data

May 11, 2017 (DE) .................. 10 2017 110 269

(51) Int. Cl.
| | |
|---|---|
| *G01N 21/25* | (2006.01) |
| *A61M 1/16* | (2006.01) |
| *A61M 1/36* | (2006.01) |
| *A61M 1/14* | (2006.01) |
| *G01N 21/33* | (2006.01) |
| *G01N 21/27* | (2006.01) |

(52) U.S. Cl.
CPC .......... *G01N 21/255* (2013.01); *A61M 1/14* (2013.01); *A61M 1/16* (2013.01); *A61M 1/1601* (2014.02); *A61M 1/1609* (2014.02); *A61M 1/1613* (2014.02); *A61M 1/1615* (2014.02); *A61M 1/367* (2013.01); *A61M 1/3612* (2014.02); *G01N 21/33* (2013.01); *A61M 2205/3306* (2013.01); *A61M 2205/70* (2013.01); *A61M 2205/702* (2013.01); *A61M 2230/20* (2013.01); *G01N 21/274* (2013.01); *G01N 2201/121* (2013.01)

(58) Field of Classification Search
CPC ... G01N 21/255; G01N 21/33; A61M 1/1601; A61M 1/1609; A61M 1/1613; A61M 1/1615; A61M 1/3612; A61M 1/14; A61M 1/16
USPC .......................................... 356/39
See application file for complete search history.

(56) References Cited

U.S. PATENT DOCUMENTS

2010/0331727 A1* 12/2010 Lindgren .......... A61B 5/14528
600/582
2014/0296766 A1 10/2014 Krause et al.

FOREIGN PATENT DOCUMENTS

| DE | 102013101523 A1 | 8/2014 |
|---|---|---|
| DE | 102013103221 A1 | 10/2014 |
| EP | 2163271 A1 | 3/2010 |

(Continued)

OTHER PUBLICATIONS

Extended European Search Report for European Application No. 18 170 606.0, with English translation, dated Sep. 7, 2018—16 pages.

(Continued)

*Primary Examiner* — Roy M Punnoose
(74) *Attorney, Agent, or Firm* — RatnerPrestia

(57) ABSTRACT

A method and device for linearizing an optical sensor in a dialysis apparatus. The method includes introducing a sensor to the dialysate-side drain line, determining the linear range of the optical sensor, backwards extrapolating the data from the linear range and correcting the data from the non-linear range.

16 Claims, 5 Drawing Sheets

(56) References Cited

FOREIGN PATENT DOCUMENTS

EP    2163272  A1    3/2010
EP    2783716  A1    10/2014

OTHER PUBLICATIONS

Uhlin et al., Complementary Parameter for Dialysis Monitoring Based on UV Absorbance, Hemodialysis International, 2009, vol. 13, pp. 492-497.
German Search Report for German Application No. 10 2017 110 269.8, dated Jan. 3, 2018 with translation, 24 pages.

* cited by examiner

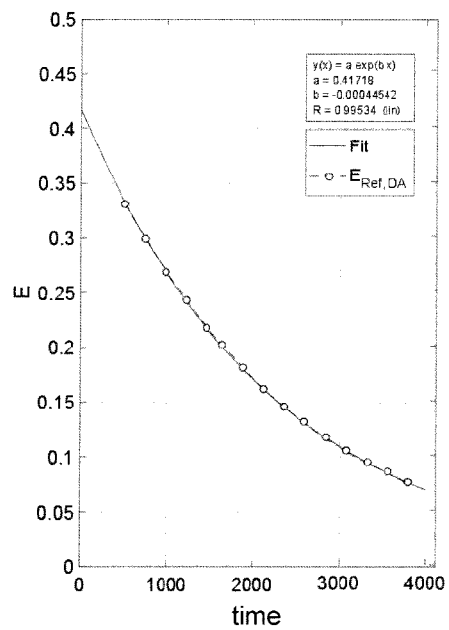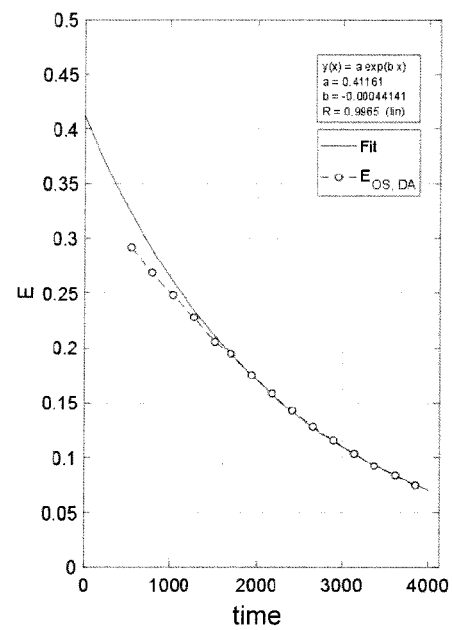
Fig. 7A    Fig. 7B
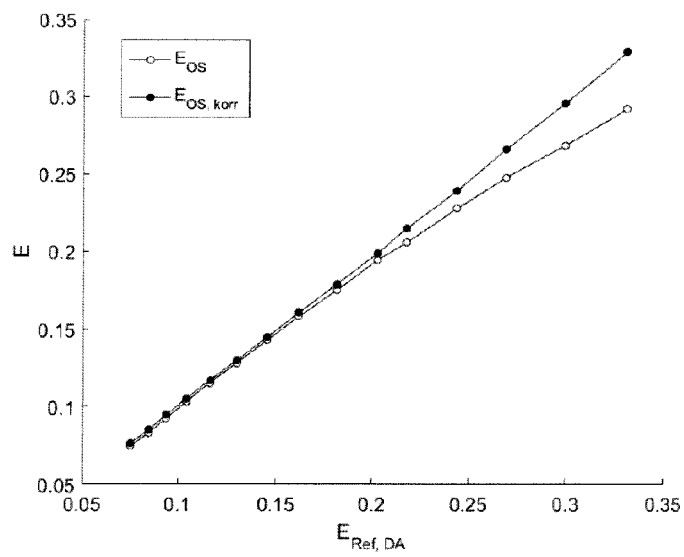
Fig. 8

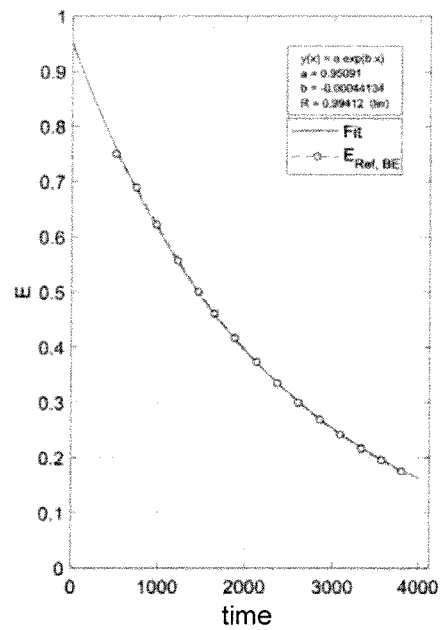
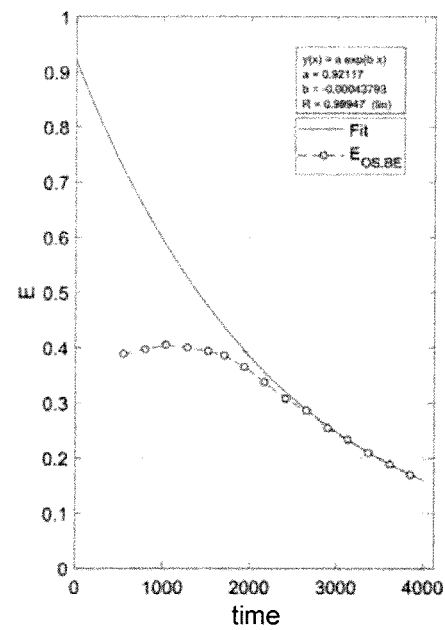
Fig. 9A          Fig. 9B
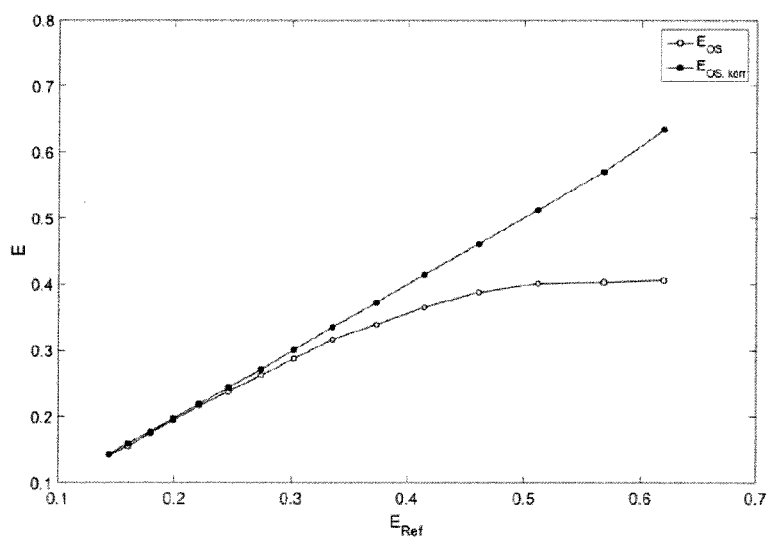
Fig. 10

ONLINE LINEARIZATION OF AN OPTICAL SENSOR

CROSS REFERENCE TO RELATED APPLICATIONS

This application claims priority to German application DE 10 2017 110 269.8 filed May 11, 2017, the contents of such application being incorporated by reference herein.

FIELD OF THE INVENTION

The invention relates to a method which determines by an optical sensor in a dialysate-side drain line and by repeated changes to the shunt whether and, respectively, when the sensor is provided in the linear range, as well as to a device for linearizing the optical sensor. By backward extrapolation of the data from the linear range the initial data that were recorded in the non-linear range can be corrected.

BACKGROUND OF THE INVENTION

A parameter for determining the dialysis efficiency is the Kt/V value. In this context, K [ml/min] is the clearance (fictitious plasma volume which is freed from a particular substance per time unit, in other words a concentration of a substance) and is determined via the urea content before and after dialysis. Moreover, t [min] is the effective dialysis time, in other words the duration of therapy. V [ml] indicates the urea distribution volume, in other words 60% of the body mass (weight) in which the blood can circulate (body fluid content). Alternatively, the clearance K or the ratio of clearance to the distribution volume K/V also constitutes an indicator for the efficiency of an ongoing dialysis treatment.

In optics, the extinction constitutes a measure for the attenuation of radiation (e.g. visible light) after passing a medium. The extinction is dependent on the wavelength and is a logarithmic variable. The extinction of the optical sensor $E_{OS}$ applied against the extinction of a reference device $E_{REF}$ (see FIG. 1) up to a particular value approximately corresponds to a straight line and after that the characteristic line flattens out. This means that the characteristic line applied against a reference flattens out with an increasing concentration of light-absorbing substances. In FIG. 1, the extinction of the optical sensor $E_{OS}$ is applied against the extinction of a reference device $E_{REF}$, the reference device including a wide linear range. In addition, the identity is evident here. Accordingly, the optical sensor is linear up to an extinction of about 0.2 and after that flattens out.

In the course of a dialysis therapy, an afore-mentioned behavior can equally be observed. This is especially applicable when a dialysate contains a plurality of light-absorbing substances, which is the case especially at the beginning of dialysis. FIG. 2 exemplifies the time course of the extinction both for the optical sensor and for the reference device. Here the two extinction characteristics are applied vis-à-vis the measuring period (in seconds). The difference between the two extinctions is relatively large especially at the beginning. In the further course, the curves are approaching each other, however, which is due to the decrease of light-absorbing substances. The optical sensor is provided in the linear range as soon as both characteristic lines lie on top of each other. In other words, especially at the beginning the outlet-side dialysate is strongly polluted, e.g. by urea or other uremic toxins. In this case, the extinction is very high and the sensor thus is provided in the non-linear range entailing very high uncertainty of measurement. With an increasing duration of dialysis, the pollution strongly decreases and the sensor enters the linear range in which the measuring values are in conformity with the measuring values of the reference device again.

In the daily routine of a hospital, a reference device having a wide linear measuring range usually is not available. Therefore, it cannot be stated whether or from when the optical sensor is provided within the linear range, and hence whether or from when the optical sensor behaves in such way as it should behave according to the reference device.

DESCRIPTION OF THE RELATED ART

Determining the Kt/V value at present is realized by various online processes. At first, the technique of "Online Clearance Measurement" is mentioned. The concept is based on the principle of electric conductivity measurement. In front of and behind the dialyzer, i.e. at the dialysis fluid inlet and the dialysis fluid outlet, two conductivity probes are installed. The conductivity within the dialysis fluid is primarily defined by the sodium concentration. The measuring technique consists in increasing the conductivity at the dialysis fluid inlet for a short time and to observe the course of conductivity at the dialysis fluid outlet. By means of the conductivity at the probes in front of of and behind the dialyzer, the sodium clearance then can be determined via the measurable difference in conductivity. Since sodium ions and urea have very similar diffusion characteristics, the sodium clearance may be directly converted to a urea clearance by which, in turn, the Kt/V value can be determined. Moreover, the distribution volume V and the treatment duration t are included in the calculation. In this technique, a measuring accuracy of +/−6% is obtained. It is a drawback of this technique that for continuous monitoring of the Kt/V value at regular intervals the conductivity at the dialysis fluid input has to be modified. In addition, the electric conductivity of electrolyte solutions is strongly dependent on further dissolved particles reducing the mobility of sodium and thus reducing the conductivity, which in turn results in wrong clearance calculations. It is another drawback of this technique that changes of conductivity may result in inadvertent intake or withdrawal of ions in the patient. Further, the change of conductivity is slow, thus rendering continuous measurement impossible.

Another technique for determining the Kt/V value consists in arranging an optical sensor at the dialysis fluid outlet and in optically detecting toxins. The method utilizes the characteristic of uric acid having maximum absorption at a wavelength of 290 nm. An optical system consisting of a UV LED which emits light at said wavelength and a photodiode which has high sensitivity in the UV range may be used to determine the quality of the uric acid concentration in the dialysate. Since the concentration of uric acid and of urea in the blood are strongly correlated, thus a decrease of the urea concentration and thus the urea clearance can be concluded from the optically determined decrease of the uric acid concentration during treatment. By means of said clearance the Kt/V value then can be calculated. It is a major drawback of this method that the sensor used has a non-linear characteristic line. In this way, the urea clearance is underestimated in the case of high load of toxins in the patient's blood and saturation of the sensor resulting therefrom. The non-linearity causes falsification, i.e. underestimation of the Kt/V calculation.

It is an object of the invention to linearize an optical non-linear sensor with respect to the measuring range at least during an ongoing dialysis therapy. Also, non-invasive determination of the clearance and of the distribution volume is possible in this way. It is a further object of the invention to project the course of the optical sensor to a virtual reference which is accompanied by an extension of the linear measuring range without modifying the hardware side of the sensor or having to adjust the sensor to a reference device.

SUMMARY OF THE INVENTION

Objects are achieved by a method and a device for linearization of an optical sensor according to the independent claims.

A method for linearizing an optical sensor in a dialysis apparatus comprises introducing a sensor in the dialysate-side drain line, determining the linear range of the optical sensor as well as backwards extrapolating the data from the linear range and correcting or replacing the data established by sensor from the non-linear range which have been determined in said non-linear range by means of the optical sensor. The method enables the measuring range to be extended without any additional components, thus resulting in reduced costs. Moreover, the Kt/V calculation is optimized. The invention further allows to determine blood-side values which are usually further comprising very high extinction values.

The backward extrapolation is carried out by non-linear regression of a regression curve. In other words, a non-linear regression is used to conclude on values provided within the non-linear range from values provided within the linear range, wherein the non-linear range is given at the beginning of measurement and the linear range is given after a measuring period to be determined.

Determining the linear range of the optical sensor preferably comprises adjusting a shunt interval having a particular shunt duration. A shunt is given when the dialysis fluid flows past the dialyzer or is stopped by an appropriate valve control. The shunt duration indicates how long a shunt takes place, in other words over which period the dialysis fluid flows past the dialyzer and thus bridges the dialyzer, or is alternatively stopped. A shunt period is a time period after which an operation, i.e. the shunt, is repeated. In other words, a shunt period is the time from the start of a shunt to the next start of another shunt. The shunt interval indicates the duration from one end of a shunt up to the start of the next shunt. A shunt duration indicates how long it is changed to a shunt.

Determining the linear range preferably comprises applying a difference of local shunt maximums and extinction signals of the optical sensor 8 directly before changing to the shunt to the extinction signals directly before changing to the shunt and determining the extinction which is smaller than a maximum turning point.

Preferably, the shunts have a first duration, especially preferred 18 seconds or less, and the shunt interval has a second duration which is longer than the first duration, preferably 4 minutes. In other words, the shunt duration is substantially shorter than the interval between the shunts. In this context, it is referred to the fact that currently "first duration" is meant to be the duration of the shunt and the "second duration" is meant to be the time interval between two directly successive shunts or shunt durations.

The shunt intervals, the shunt durations and thus the shunt periods may be distributed to be equidistant or non-equidistant in time. In other words, the shunts may occur regularly, which allows certain measuring results over the entire measuring range, or they may occur irregularly, which allows higher measuring accuracy with an expected turning point between the linear and the non-linear behavior with a larger number of shunts, i.e. measuring points, in a shorter period of time.

The shunt intervals or shunt periods may also start as late as after a predetermined duration of therapy, which offers the advantage that only the linear range is measured and thus the duration of measurement is reduced.

The clearance K is preferably calculated by calculation of the extinction in the plasma or plasma water, preferably after a shunt maximum following a shunt duration which ranges from 2 to 3 minutes. In the reverse conclusion this means that the determination of the dialysate-side clearance and of the blood-side clearance can be performed. In other words, the blood-side clearance can be non-invasively determined.

Preferably, the method further comprises determining a Kt/V value, especially by way of a regression curve. The Kt/V value may be used for inspecting the linearized optical sensor. Accordingly, the Kt/V value can be calculated by determining the initial urea content c(t) and an urea concentration at a given point in time t which in turn were measured by a linearized optical sensor, by the model for considering the rebound effect or by the single-pool model taking the urea generation during therapy into account.

The linearization of the optical sensor is used in dialysis, more exactly speaking in the dialysis machine, but it is not only limited to the field of dialysis. The method may be used in all fields where the concentration of an absorbing material decreases according to an algorithm, e.g. an exponential function. The dialysis machine comprising an optical sensor for measuring the current dialysis process is further comprising a data correction unit which is adapted to linearize the optical sensor according to the afore-mentioned method.

BRIEF DESCRIPTION OF THE DRAWINGS

The invention is best understood from the following detailed description when read in connection with the accompanying drawings. Included in the drawings are the following figures:

FIG. 7A shows the dialysate-side extinction course of the reference values as well as the exponential fit of the values.

FIG. 7B shows the dialysate-side extinction course of the optical sensor as well as the extrapolating exponential fit of the last nine values, FIG. 8 shows the linearized characteristic line of the optical sensor along with the original characteristic line, FIG. 9A shows the blood-side extinction course of the reference values as well as the extrapolated fit of the values, FIG. 9B shows the blood-side extinction course of the optical sensor as well as the extrapolating exponential fit of the last four values, and FIG. 10 shows the linearized characteristic line of the optical sensor along with the non-linearized characteristic line.

DETAILED DESCRIPTION OF THE PREFERRED EMBODIMENTS

Figure 3:
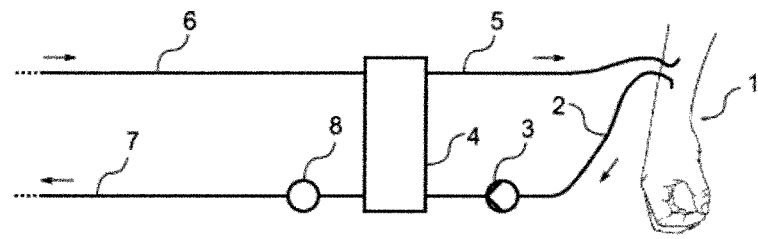
FIG. 3 shows a schematic representation of the invention.

In FIG. 3 the schematic representation of the invention is illustrated. Blood which is conveyed to a dialyzer is collected from a patient 1 via the arterial tube system 2 by means of a conveying unit 3. In the dialyzer 4 the blood is freed from urinary excreted substances and excess water. Subsequently, the purified blood is returned to the patient via the venous tube system 5. The collection and the return of the blood via a joint cannula is equally imaginable. In the dialyzer 4 hollow fiber capillaries are provided which have a semipermeable membrane. The capillaries are flushed by the so-called dialysis fluid which, on the one hand, absorbs urinary excreted substances and excess water from the blood and, on the other hand, outputs especially hydrogen carbonate for treating an acidosis of the patient 1. The dialysis fluid flows through the feed line 6 to the dialyzer. At the dialysis fluid outlet of the dialyzer 4 a drain line 7 comprising at least one optical sensor 8 is arranged. The optical sensor 8 comprises at least one photodiode and preferably two photodetectors and is used for determining an absorption characteristic of a dialysate. This is preferably the absorbance or, respectively, extinction which can be measured when the dialysate includes substances which absorb light. The photodiode of the optical sensor 8 for this purpose emits narrow-band light in the UV range with the wavelengths between 200 and 350 nm being preferred. Preferably, light having a peak wavelength of from 275 and 295 nm is emitted. Alternatively, the optical sensor is designed so that it measures fluorescence, to which end it emits light for exciting optically active substances and then measures the emission.

Different options are resulting for the position of the optical sensor 8 in the drain line 7. For example, in the case of a shunt it may be located in the separated part and/or in front of a balancing device or behind a balancing device.

Figure 1:
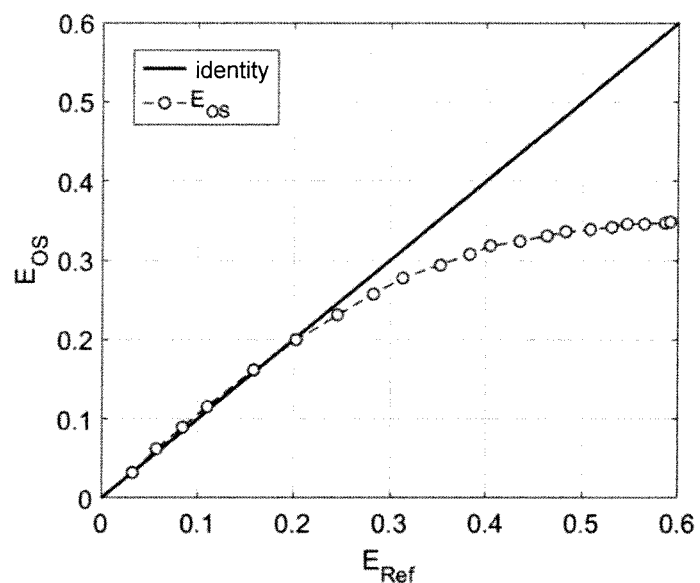
FIG. 1 shows the extinction of an optical sensor with respect to a reference device.
Figure 2:
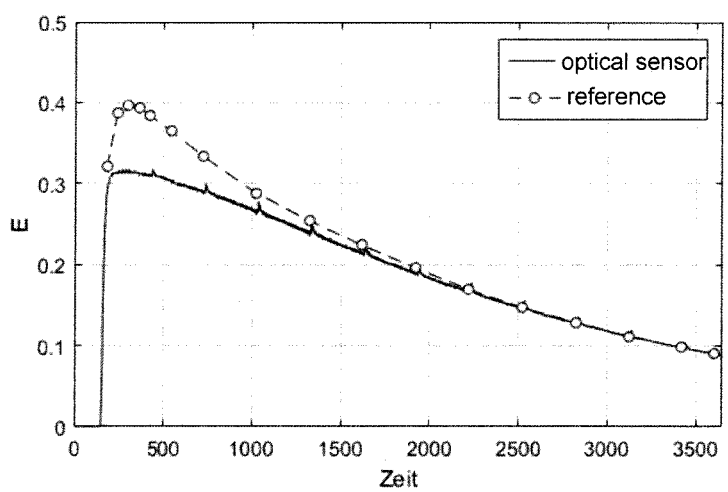
FIG. 2 shows the time course of extinction both for the optical sensor and for the reference device.

Frequently, the characteristic line of the optical sensor 8 is linear to a limited extent only (see FIG. 1). In order to extend the linear measuring range, according to aspects the invention it is repeatedly changed to the shunt in the course of therapy. During the shunt, the dialysis fluid flows through an appropriate valve position past the dialyzer, wherein the blood continues being conveyed through the dialyzer 4. Due to stopping (or alternatively at least reducing) the dialysis fluid flow through the dialyzer 4, at least part of the dialysis-side residual volume is at least partially saturated. I.e. substances, and especially light-absorbing substances, on the blood side pass over to the enclosed dialysate side, in other words in the dialyzer substances interacting with electromagnetic radiation pass from the blood-guiding side over to the dialysis fluid-guiding side. Of preference, shunt durations of 18 seconds are provided. Also, the reverse that substances pass from the enclosed side over to the blood side is possible.

Figure 4:
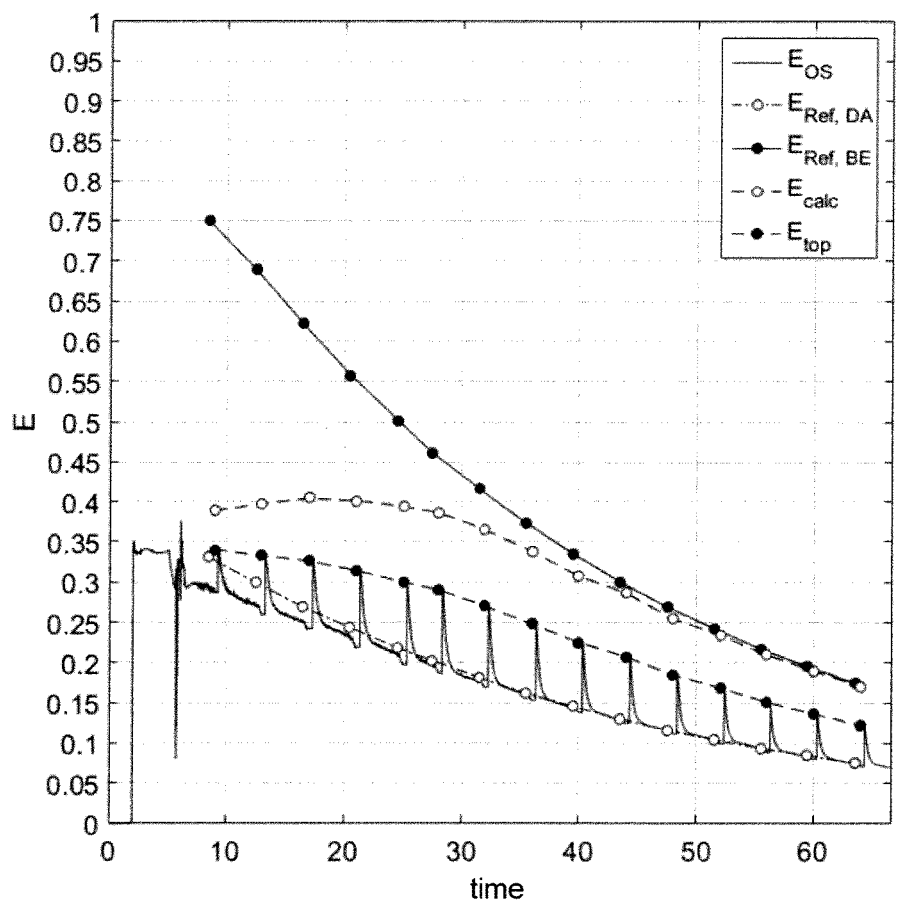
FIG. 4 shows a course of extinction during therapy.

In FIG. 4 an extinction course during a therapy is illustrated. At an interval of four minutes, it is changed to the shunt for 18 seconds at a time. The extinction signal of the optical sensor 8 ($E_{OS}$) shows a short-time increase after stopping the shunt. The local maximums are referred to as $E_{top}$. $E_{Ref,DA}$ denotes the course of extinction at the dialysis fluid outlet measured by a reference device. $E_{Ref,BE}$ denotes the course of extinction at the blood inlet measured by a reference device. $E_{calc}$ denotes the course of extinction at the blood inlet measured by an optical sensor.

Figure 5:
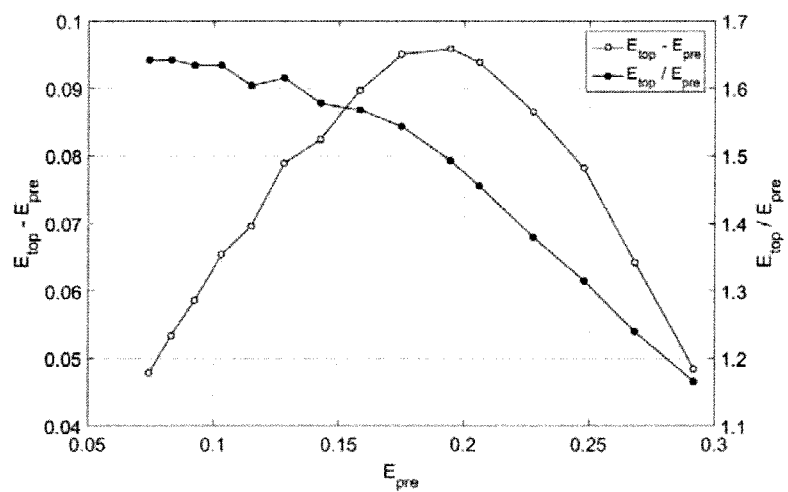
FIG. 5 shows the extinction difference of an optical sensor.
Figure 6:
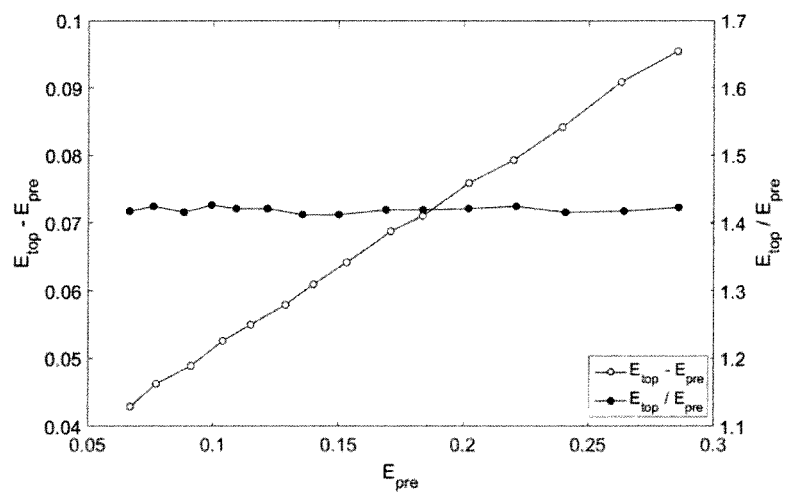
FIG. 6 shows the extinction difference of a reference measuring device.

Solely on the basis of the curve $E_{OS}$ it is not evident whether or, respectively, when the optical sensor is linear. When, however, the difference $E_{top}-E_{pre}$ is applied over $E_{pre}$ (with $E_{pre}$ standing for the extinction of $E_{OS}$ shortly before changing to the shunt), a characteristic curve is resulting, as shown in FIG. 5. In a linear sensor the difference $E_{top}-E_{pre}$ applied over $E_{pre}$ would be a monotonically increasing straight line (see FIG. 6). In the case of the optical sensor, the difference shows a maximum turning point, however, and then decreases again. The $E_{pre}$ value in the maximum turning point represents the extinction from which the optical sensor becomes non-linear. Extinctions smaller than the $E_{pre}$ value in the maximum turning point thus are trustworthy as regards linearity. In other words, extinctions above the maximum turning point originate from the non-linear range and there below originate from the linear range. In each of the figures, also the $E_{top}/E_{pre}$ ratio is shown against $E_{pre}$. In the case of the reference measuring device the ratio is constant. In the case of the optical sensor, a constancy for $E_{pre}$ values smaller than the $E_{pre}$ values in the maximum is valid. The ratio is continuously decreasing for increasing values. Thus, instead of the difference, also the ratio may be considered so as to be able to judge whether and, respectively, from when the sensor is within the linear range.

The course of the difference in FIG. 5 may be considered a downward opened parabola. As is known, a parabola is mathematically defined by three points. Thus, it is also imaginable to reduce the number of circuits in the shunt to at least three, for example at the beginning of a therapy, in the middle of a therapy and at the end of a therapy. By a subsequent square fit through said at least three points the vertex of the parabola can be determined which can be considered to be a linearity limit, as described before.

The invention provides as an alternative to restrict the implementation of the shunt changes to the non-linear range only, i.e. at the beginning of therapy. In randomly defined time intervals it is changed to the shunt and subsequently the difference is observed. As soon as a flattening or the reversal of the gradient of the curve is detected, subsequent changes to the shunt can be renounced, as the sensor is linear from this point. The range within which changing to the shunt would occur, would correspond to the right leg of the parabola in FIG. 5.

For linearization $E_{pre}$ values that are smaller than the $E_{pre}$ values in the maximum are used. Said values now are used for non-linear regression. Preferably, this is an exponential function of the formula:

$$E(t)=a \cdot e^{bt}$$

However, also other functions such as a double exponential function, for example, are imaginable.

FIG. 7A illustrates a regression for the reference measuring device. It is clearly visible in which way the measuring data and the regression curve lie on top of each other. The extrapolated extinction at t=0 is just above 0.4. FIG. 7B illustrates a similar representation. However, here the values of the optical sensor are shown. It is evident how in this case the measured extinction values deviate from the regression curve at an extinction of about 0.2. When the last nine data are fitted and extrapolated, the extinction at t=0 just as the reference is at a value of slightly above 0.4. Thus, the reference and the fit of the optical sensor show identical curves. Hence the optical sensor 8 is online linearized during measurement.

In FIG. 8 now the characteristic line of the optical sensor linearized according to aspects of the invention is shown ($E_{OS,korr}$). In addition, the original characteristic ($E_{OS}$) is applied which had to be corrected.

The time interval of the changes to the shunt is variable. It may be implemented at fixedly defined intervals during the entire therapy duration, for example, wherein the times of changing to the shunt may be distributed to be equidistant or non-equidistant. Moreover, it is imaginable that changes to the shunt start as late as after or up to a particular duration of therapy.

Since the initial values (extinction at t=0) and the extinction values at the end of a therapy are known now, the Kt/V value can be corrected according to any one of the following equations.

A simplified model without considering further effects is the simplest formula for determining the Kt/V value during dialysis therapy. It takes neither the generation of urea in the patient during therapy nor the so-called rebound effect into account.

$$\frac{Kt}{V} = \ln\left(\frac{c_0}{c(t)}\right)$$

Here K stands for the urea clearance, t stands for the duration of therapy, V stands for the urea distribution volume, $c_0$ stands for the initial urea concentration and c(t) stands for the urea concentration at a given point in time t.

Another model for determining the Kt/V value is the Single-Pool model taking urea generation during therapy into account. In this model it is assumed in a simplified manner that urea is dissolved merely in a large distribution volume. As compared to the afore-mentioned model, it is considered that during therapy urea is generated in the patient's body. Moreover, the model considers that the convection occurring by ultrafiltration additionally removes urea.

$$sp\frac{Kt}{V} = -\ln\left(-0.008 \cdot t + \frac{c(t)}{c_0}\right) + \left(4 - 3.5 \cdot \frac{c(t)}{c_0}\right) \cdot \frac{UF}{W}$$

UF stands for the ultrafiltration volume and W stands for the patient's weight.

Another model for determining the Kt/V value considers the rebound effect (equilibrated Kt/V). In reality, the movement of urea through the body is not unrestrictedly possible, as urea is present both in the intracellular and in the extracellular space and in the intravascular space. A model considering the existence of said different spaces deviating from the Single-Pool model helps to determine a so-called equilibrated Kt/V. In this case, the backflow of urea after therapy from organs of low blood flow into the intravascular space is taken into consideration.

$$e\frac{Kt}{V} = sp\frac{Kt}{V} - \frac{0.6}{T} \cdot sp\frac{Kt}{V} + 0.03$$

In this formula, T corresponds to the entire duration of therapy.

Especially toward the end of the dialysis therapy, the extinction to be expected is low, as many light-absorbing substances have been removed already. Therefore, it is provided to implement a long shunt of about 2 to 3 minutes especially toward the end of therapy. During a shunt, the dialysis fluid flows past the dialyzer, with the blood continuing to circulate. After a certain period of time the dialysate-side residual volume in the dialyzer absorbs the substances from the blood to the extent that an at least partially diffusive equilibrium exists between the dialysate side and the blood side in the dialyzer. When it is changed to main connection again, the saturated dialysate-side residual volume is guided through the optical sensor 8, where a short-time signal change can be measured. The extinction in the maximum of the signal change corresponds to the extinction in the plasma or at least in the plasma water. For calculating the extinction in the plasma and, respectively, in the plasma water the following equation is used:

$$E_{calc}=(E_{top}-E_{pre}) \cdot k + E_{pre}$$

wherein the factor k in the case of long shunt is 1. The clearance K can be determined according to the following equation, as is known:

$$K = Q_d \cdot \frac{C_{Do}}{C_{Bl}}$$

Here $Q_d$ stands for the dialysis fluid flow and $C_{DO}$ as well as $C_{BI}$ stand for concentration-equivalent variables at the dialysis fluid outlet and the blood inlet. A concentration-equivalent variable for example is a concentration of one or more substances or an absorption characteristic such as the absorbance or, respectively, extinction or fluorescence. According to Beer-Lambert' law, the extinction is proportional to the concentration of a light-absorbing substance. $C_{DO}$ may be determined directly by means of the optical sensor 8 ($C_{DO}=E_{OS}$). $C_{BI}$ is resulting from the local maximums that occur following a shunt and are calculated as afore-described ($C_{BI}=E_{calc}$).

It is obvious that blood-side extinctions are always higher than dialysate-side extinctions so that the change to the shunt limited in time up to reaching a diffusive equilibrium always or at least very frequently would take sensor signals to the non-linear range. In the worst case, the optical sensor would be in saturation, which hardly allows any informative measurements. Laboratory measurements have resulted in the fact that a shunt duration of 18 seconds is sufficient to subsequently reach 50% of the blood-side value. The risk of the optical sensor being provided in saturation is significantly reduced in this way. Related to the equation for calculating the extinction in the plasma, this means that k=2 is required. If other dialyzers or flow rates are used, the invention provides to determine the factor online. For this purpose, at first a long shunt and subsequently a short shunt are implemented, and alternatively first a short one and subsequently a long one. Finally, from both shunts the ratio $$k = \frac{(E_{top} - E_{pre})_{lang}}{(E_{top} - E_{pre})_{kurz}}$$

is formed, wherein the numerator originates from the long shunt and the denominator originates from the short shunt. When, in this way the k factor is determined, by way of short shunts a blood-side value ($E_{calc}$) is non-invasively determined by dialysate-side measurements. Of course, it is further also possible to select even shorter shunt times, which equally results in an adaptation of the k factor. Shorter shunt times offer the advantage that the subsequent local extinction maximums are smaller and tend to be rather within the linear range of the characteristic line of the optical sensor.

When repeatedly short shunts and at least at the end of therapy at least one long shunt are implemented, blood-side values ($E_{calc}$) can be determined by determining the k factor and the equation for calculating the extinction in the plasma. It is important for this purpose to make use of extinctions which lie within the linear range of the optical sensor. This relates especially to the extinctions $E_{top}$ and $E_{pre}$. It can be inferred from the picture in FIG. 5 which values are within the linear range. Now similarly to the preceding sections, non-linear regression curves can be drafted. FIG. 9A shows the corresponding regression for the reference and FIG. 9B shows the corresponding regression for the optical sensor. In the case of the optical sensor, the four last calculated values at the blood inlet ($E_{calc}$) were considered. In this case, too, the extrapolated values with t=0 are about equal, when comparing the reference and the optical sensor to each other. In the right-hand part of the figure it is moreover clearly evident in which way the calculated values ($E_{calc}$) deviate from the regression curve at the beginning of therapy. It is known that the number of regression points has a great influence on the quality of extrapolation. In order to design the extrapolation even more robust and more precise for this reason, in addition blood samples may be collected at the beginning and toward the end of therapy and may be analyzed so as to determine a Kt/V value by way of the equations 1, 2 and/or 3. Said Kt/V value then can be compared to the Kt/V value from the extrapolation and can be used to correct the latter.

FIG. 10 shows the linearized characteristic line of the optical sensor along with the non-linearized characteristic line. In the equation for non-linear regression the variable b stands for the ratio of clearance K to the distribution volume V:

$$b = \frac{K}{V}$$

Since b can be determined from fits (see FIGS. 7A, 7B, 9A, and 9B) and K is calculated according to the equation for calculating the clearance, the equation for calculating the variable b can be rearranged for V. In this way, the distribution volume can be determined.

Since, for the first time, retroactive correction is made, the course of the optical sensor can be corrected already during therapy, i.e. online. For this, e.g. the characteristic lines from FIG. 8 and FIG. 10 can be used. Moreover, the invention provides to store at least the maximums of the difference $E_{top}-E_{pre}$ over $E_{pre}$. In this way, it can be predicted with sufficiently available data for following therapies whether, respectively, from when the sensor data are within the linear range. This helps to avoid changes to the shunt at the beginning of therapy.

Alternatively, an embodiment without any additional recording of measuring values is imaginable. The characteristic line of the optical sensor 8 (or of any other sensor) is deposited on the machine and/or a data managing system. This may be realized, for example, in the form of a look-up table and may be used for adjusting the optical sensor 8 during an ongoing therapy. In this way, too, changes to the shunt can be avoided or at least reduced. Since each change to the shunt results in the fact that the blood cannot be sufficiently purified for this period, it is of advantage to carry out, during a shunt, further measurements or tests which equally require changing to the shunt so as to make efficient use of the time for multiple applications.

The invention claimed is:

1. A method of linearizing an optical sensor in a dialysis apparatus, comprising the steps of:
   introducing the optical sensor to a dialysate-side drain line of a dialysate circuit,
   determining a linear range of the optical sensor,
   recording data with the optical sensor in a linear range and a non-linear range,
   backwards extrapolating the recorded data recorded in the non-linear range by the data recorded in the linear range,
   correcting or replacing the data determined by the sensor from the non-linear range with the backwards extrapolated data for the non-linear range.

2. The method according to claim 1, wherein the backward extrapolation is implemented by non-linear regression of a regression curve.

3. The method according to claim 1, wherein the method further comprises the step of:
   adjusting a shunt interval and shunt duration of a shunt in the dialysate circuit.

4. The method according to claim 3, wherein determining the linear range further comprises the steps of:
   applying a difference of local shunt maximums as minuend and extinction signals of the optical sensor before changing to the respective shunt as subtrahend to the extinction signals before changing to the shunt as abscissa axis and determining at least one extinction or where the data is smaller than a maximum turning point.

5. The method according to claim 4, wherein the shunt maximums of the difference are stored.

6. The method according to claim 5, wherein the shunt intervals start after a predetermined duration of therapy.

7. The method according to claim 3, wherein the shunt has a first duration of 18 seconds and the shunt interval has a second duration longer than the first duration.

8. The method according to claim 7, wherein the first duration is 18 seconds or less and the second duration is 4 minutes.

9. The method according to claim 3, wherein the shunt intervals are distributed to be equidistant or non-equidistant in time.

10. The method according to claim 3, wherein the determination of a clearance K is carried out by calculating the extinction in the plasma, after a shunt maximum following a shunt duration between 2 and 3 minutes.

11. The method according to claim 10, wherein the determination of a dialysate-side clearance and of blood-side clearance is non-invasive.

12. The method according to claim 1, wherein the method further comprises the step of:
   determining a Kt/V value for checking the linearization of the optical sensor.

13. The method according to claim 12, wherein calculating the Kt/V value is carried out by determining an initial urea content and a urea concentration c(t) at a given point in time t, which were measured by a linearized optical sensor.

14. The method according to claim 12, wherein the determined Kt/V value is determined by a model for considering a rebound effect.

15. The method according to claim 12, wherein the determined Kt/V value is determined by a Single-Pool model with consideration of the urea generation during therapy.

16. A dialysis machine comprising:
an optical sensor for measuring a current dialysis process; and
a data correction unit adapted to linearize the optical sensor according to a method in accordance with claim 1.

* * * * *